United States Patent [19]
Johnson et al.

[11] Patent Number: 6,071,981
[45] Date of Patent: Jun. 6, 2000

[54] ANTI-IMMUNORESPONSIVE POLYMERIC MATERIAL AND ITS USE IN BIOLOGICAL APPLICATIONS

[75] Inventors: Dee Lynn Johnson, St. Paul; William A. Hendrickson, Stillwater, both of Minn.

[73] Assignees: Aveka, Inc., Woodbury; Techmatch, Inc., St. Paul, both of Minn.

[21] Appl. No.: 09/163,725

[22] Filed: Sep. 30, 1998

Related U.S. Application Data
[60] Provisional application No. 60/060,459, Sep. 30, 1997.

[51] Int. Cl.[7] .............................. C08J 3/00; C08K 5/34; C08L 89/00; C08L 1/00; A61K 9/14

[52] U.S. Cl. .................... 523/105; 424/486; 424/488; 524/22; 524/31; 524/35; 524/86; 524/96; 524/104

[58] Field of Search .................. 524/22, 31, 35, 524/86, 96, 104; 523/105; 424/486, 488

[56] References Cited

U.S. PATENT DOCUMENTS

| | | | |
|---|---|---|---|
| 3,508,941 | 4/1970 | Johnson | 106/126 |
| 4,255,300 | 3/1981 | Franks et al. | 536/56 |
| 4,795,542 | 1/1989 | Ross et al. | 204/403 |

*Primary Examiner*—Patrick D. Niland
*Attorney, Agent, or Firm*—Schwegman, Lundberg, Woessner & Kluth, P.A.

[57] ABSTRACT

A polymer composition comprising an anticoagulant carried in a water soluble polymer hydrogen bonded to a cellulose polymer. The composition is useful as sutures, implantable material, temporary grafts, vasculature connections and the like. The composition can be prepared by a method comprising the steps of: forming a solution in an amine oxide of a water-soluble polymer capable of hydrogen bonding, a cellulose polymer, and an anticoagulant and reducing the amount of amine oxide in the solution to solidify a solid polymer composition comprising the anticoagulant in the water soluble polymer and the cellulose polymer. The polymer compositions are particularly useful in temporary implants, sutures, grafts or the like.

29 Claims, 2 Drawing Sheets

ANTI-IMMUNORESPONSIVE POLYMERIC MATERIAL AND ITS USE IN BIOLOGICAL APPLICATIONS

This application claims the benefit of U.S. Provisional Application Ser. No. 60/060,459, filed Sep. 30, 1997.

BACKGROUND OF THE INVENTION

1. Field of the Invention

The present invention relates to polymeric materials, particularly biocompatible polymeric materials which can be used in biological applications such as wound dressings, artificial skin, tissue encasement or replacement and vascular replacement or repair.

2. Background of the Art

One of the more significant limitations in the practice of medical procedures which implant replacement materials or protect exiting materials within the body is a limitation on the supply and amount of materials which can be used within living tissue without damage to the patient or tissue, or stimulation of immune responses within the body. There are basically three classes of materials which are considered biocompatible and used in medical procedures. Inert inorganic materials (such as Nitonol™ metal, titanium, inorganic oxides [especially as ceramics]), organic synthetic polymers which attempt to replicate naturally occurring organic materials (e.g., polyamides), composites; and harvested natural tissues and materials (e.g., veins, arteries, placental tissue, corneas, etc.). Although some of these materials have generally been regarded as biocompatible, they may still stimulate immune responses, may not satisfactorily replace specific biological materials for which substitution is needed, or (in the case of harvested materials) may cause collateral damage to the patient (as in by-pass surgery with self-donated vasculature).

Although more than three hundred thousand by-pass surgeries are performed each year, there are approximately another three hundred thousand patients for whom the surgery would be beneficial, but for whom the surgery is not available. At least one reason why this surgery can not readily be performed on these potential patients, many of whom are women, is the fact that their vasculature tends to be relatively smaller, which small size does not lend the patient's system to this type of surgery. Especially where relatively small vasculature from one part of the body (e.g., the normal selection of material from the inseem of the thigh) must be used to replace veins and arteries around the heart (which tend to be relatively large), the limitations in size available can dictate against the surgery.

U.S. Pat. No. 4,411,893 describes topical therapeutic compositions which comprise 0.1 to 70 percent by weight of a water-soluble tertiary amine oxide and a therapeutic agent selected from erythromycin, benzoyl peroxide, hydrocortisone, tetracycline, 5-fluorouracil and propranolol. The amine oxide is described as enhancing the penetration of the therapeutic agent through the skin. Hydrophilic polymer additives such as acrylic polymers, polyvinyl alcohol, gelatin, hydroxyethyl cellulose, carboxymethyl cellulose, natural gums and other thickening agents are also described.

U.S. Pat. No. 3,508,941 describes a method of preparing polymers from a mixture of cyclic amine oxides and other polymers. Two different polymers, which may be selected from a wide range of natural and synthetic polymers, are dissolved together in a common solvent and then precipitated from the cosolution. It is asserted that there may be chemical reactions between the constituent polymers, which reactions create physical properties different from those of the either of the individual polymer components. In addition, the polymers may be physically joined by strong interpolymer hydrogen bonding. The polymers, for example, may be selected from amongst those a) having the capacity for strong intermolecular bonding and those b) which have the same or similar capacity or polymers having less than but at least some capacity for intermolecular hydrogen bonding. Polymers generally described include, for example, those containing atoms from Groups V-A or VI-A of the periodic table, preferably with nitrogen atoms in amine or amide groups, and/or oxygen atoms such as in carbonyl groups, hydroxyl groups, ether groups and the like. Typical polymers within this generic disclosure include, for example, poly (vinyl acetates), poly(vinyl alcohols), poly(esters), poly (saccharides, cellulose, starch, poly(anhydroglucose), poly (diethylaminoethylanhydroglucose), gum arabic, poly (amides), poly(vinylpyrrolidones), polymeric proteins or polypeptides (such as wool, silk, gelatin, hair, and the like), etc. The amine oxide is preferably cyclic mono(N-methylamine-N-oxide.

U.S. Pat. No. 2,179,181 (Graenacher et al.) describes the use of oxides of ternary amines, including heterocyclic amines, to dissolve cellulose.

Manufacturing information on Tencel™ fibers which is provided by Courtalds Corporate Technology, Coventry, England indicates that this fiber material is produced by direct solvent spinning procedures from amine oxides, such as NMMO, N-methylmorpholine-N-oxide. The process is taught to provide a highly oriented cellulose fiber in an environmentally benign manner. The amine oxide solvent is readily recoverable from the process, as the dissolved polymer is extruded into water, with the NMMO being readily recoverable from the water and having extremely low volatility.

BRIEF DESCRIPTION OF THE INVENTION

Biocompatible, and more particularly haemocompatible, polymeric materials comprising an anticoagulant carried in a medium comprising cellulosic polymer and water-soluble polymer in a hydrogen bonded association are both anti-thrombotic and biocompatible, and may be used in tissue replacement events and then safely dispersed by normal hydrolysis of the components within the patient. The cellulosic polymer and water-soluble polymer are codissolved in an amine oxide, which is preferably a cyclic mono(N-methylamine-N-oxide, such as N-methylmorpholine-N-oxide, along with the anticoagulant, and the polymeric material formed by then conventional means into film or structure (e.g., extruded shapes, tubes, gaskets, valves, patches, etc.) which may be implanted in or affixed to a patient. Particularly where heparin is used as the anticoagulant, the heparin can also hydrogen bond to the cellulose and/or water-soluble polymer, keeping the heparin within the composition for a controlled amount of time.

DETAILED DESCRIPTION OF THE INVENTION

Figure 1A:
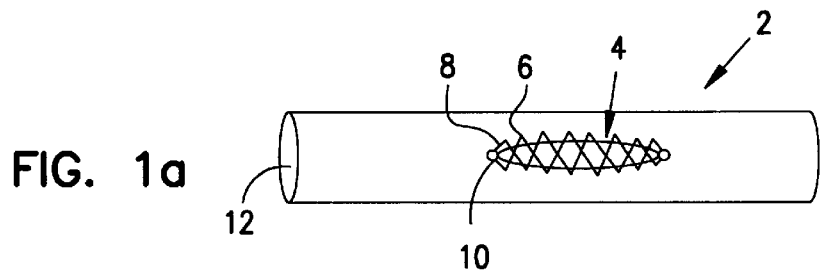
FIG. 1 shows a series of elements and conditions of those elements in the preparation and surgical application of a vascular closure. 1a shows a vascular closing element with a hole and loose prestitching. 1b shows the stents used with the closure element. 1c shows the stents positioned within the closure element. 1d shows the stents, closure element and suturing of the element to the vasculature. 1e shows the sutured element on the vasculature with the stents removed but the prestitching still untightened. 1f shows the completed application of the closure element on vasculature.
Figure 1B:
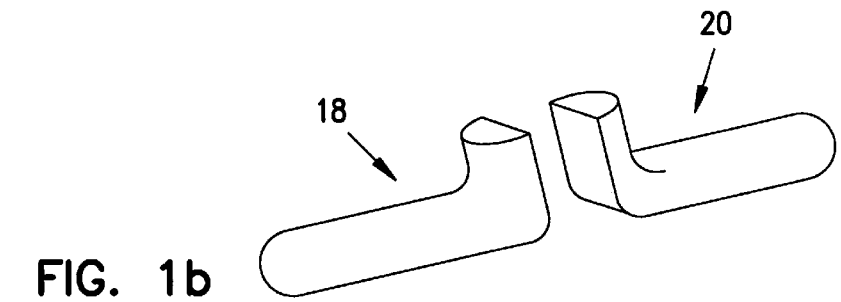

Some medical procedures require the implantation of materials into the patient to support or repair structural damage to the patient, whether simply exterior sutures, or internal repair such as interior sutures, mesh reinforcement, film reinforcement, structural replacement (e.g., arteries, veins, or other vascular replacement), valves, organ walls, and the like. Many of these procedures require only that the added material persist for a short period of time while the body heals and natural defenses and repairs occur. It is desirable in those instances to have a material which is both biocompatible when inserted and then dissolves to form a harmless residue which may be carried away or absorbed by the body. The natural immune responses of the body prevent a wide range of materials from satisfactorily performing this function, and the use of materials which have known low levels of immuno-response stimulation (such as cellulose polymers and gelatin) is a desirable goal.

The present invention describes a polymeric composition and polymeric articles comprising a polymer matrix of cellulosic polymer in hydrogen-bonded association with a water-soluble polymer, with the polymer matrix carrying an anticoagulant effective amount of an anticoagulant. These materials may be biocompatible, and more particularly haemocompatible (compatible with use in the blood circulatory system of animals, especially humans, without creating harmful levels of coagulation within the system).

The cellulose polymer component may be any cellulose polymer, natural or synthetic, which may be dissolved in an amine oxide. Natural cellulose polymers, such as cotton, plant fiber (from stalk, leaf, fruit, vegetable or grain, including processing residue), and the like. Synthetic polymer such as rayon, ramie, and the like may also be used, as long as the polymer is capable of being codissolved in an amine oxide solvent (even at elevated temperatures, e.g., above 50° C.) with the water-soluble polymer and the anticoagulant. The cellulose polymer comprises from about 20% or 30 to 91% by weight of the total solids in the polymer composition (considering the cellulose polymer, the water soluble polymer and the anticoagulant).

Preferably the cellulose polymer comprises from 20, 30 or 40% up to about 91%, more preferably from 50 to 91%, still more preferably from 60, 70 or 80% to 91% of the solids in the polymer. Even with high percentages of water-soluble polymer present in the composition, the hydrogen bonding between the cellulose polymer and the water-soluble polymer keeps a level of control over the rate of dissolution or hydrolysis of the polymer composition. Even if the polymer hydrolyzes fairly quickly, the components of the polymer composition (the cellulose polymer and the gelatin) are readily absorbed into the blood stream and are easily handled by the normal functioning capabilities of the body's digestive and waste carrying systems.

The water soluble polymer may be selected from a wide range of natural and synthetic polymer. It is important that the polymer be capable of hydrogen bonding with the cellulose polymer to form a stable composition with the cellulosic polymer. Hydrogen bonding in the practice of the present invention is the interaction between two functional groups in different molecules. One of the functional groups acts as a proton donor (e.g., as an acid) or proton contributor (without complete disassociation of the hydrogen) and the other molecule must provide a functional group which acts as a proton acceptor, electron donor (e.g., a base) or electron contributor (without complete acceptance of a proton or loss of the electron). A proton is most often contributed by a carboxyl, hydroxyl, amine or amide group, or may be a proton attached to a halogen or sulfur atom. Functional groups which may contribute an electron may include the oxygen atom in carboxyls, ethers and hydroxyls, the nitrogen atoms in amines and N-heterocyclic compounds. A hydrogen bond can be generally considered as an interaction between a functional group A—H and an atom or group of atoms B in a different molecule where there is evidence of bond formation in which a new bond linking of A—H to B is through the H atom. Evidence of this type of bonding may be obtained by common analytical techniques such as from molecular weight determinations or from spectrographic determinations. Compounds containing intermolecular hydrogen bonding exhibit different physical properties, such as different boiling and freezing points, changed dielectric properties, higher viscosities, modified electronic spectra, and different solubility characteristics. The water-soluble polymer includes polymers which are water-dispersible polymers. These materials are used to moderate the properties of the composition and allow a rate of hydrolysis of the polymer composition to be tailored for specific uses of the polymer composition. The water soluble composition may comprise, for example, from about 9.9% to 80%, 70%, 60%, 50%, 40%, 30% or 20% by weight of solids of the polymer composition based upon the cellulosic polymer, the water-soluble polymer and the anticoagulant (inclusive of the anticoagulant). The relatively greater the proportion of the water soluble polymer in the composition, the less durable or persistent the overall polymer material will be in the patient. These materials tend to be subject to hydrolysis within the aqueous blood environment of the patient and will break down, and even become metabolized over time. Depending upon the specific use to which the polymer composition will be involved, the length of time or durability of the polymer can be tailored to those specific needs. Where the water-soluble polymer is capable of being crosslinked, a low degrees of crosslinking in the polymer before dissolution may be effected, or the crosslinking agent may be initiated after formation of the polymeric article by imbibing the agent or initiating an agent already present within the composition (e.g., by thermal or radiation initiation). Where the water soluble polymer is gelatin (which is the preferred polymeric material), there are many hardening agents known within the photographic art which could be used to harden or crosslink the water soluble polymer component of the compositions of the present invention. Those agents should be selected on the basis of their suitability for use within the human body and especially within environments where the hardening agents must be haemocompatable. Some of these hardening agents are quite aggressive, and care must be exercised in their selection.

Anticoagulants are a known pharmaceutical class of compounds which delay or prevent the coagulation of blood. There are at least three different mechanisms for the performance of anticoagulants:

1. Calcium sequestering agents, heparin and heparin substitutes, and prothrombopenic anticoagulants. Calcium sequestering agents remove calcium from the local environment, and as calcium is essential to several steps in the blood coagulation process, clotting can be reduced or prevented. These agents are generally employed in only withdrawn blood, as in transfusion environments or the like.

2. Heparin and heparin substitutes complex with antithrombin III. These complexes then may interact with certain activated clotting factors, such as factors IX–XII to prevent conversion of prothrombin to thrombin. In high concentrations, the complexes interact directly with thrombin and inhibits its ability to promote conversion of fibrinogen to fibrin. The complexes also inhibit the aggregation of platelets. Heparin is the most widely used material of this class and has the particular advantage that it is a naturally occurring substance tolerated by the systems of patients.

3. Prothrombopenic anticoagulants competitively inhibit vitamin K in the hepatic production of prothrombin (factor II). The plasma content of prothrombin is thus reduced and coagulation of blood is reduced. These drugs also may suppress the formation of factors VII, IX and X, even though the effect on prothrombin is the predominant activity.

The anticoagulants which complex with antithrombin III are the preferred anticoagulants of the present invention. These materials should be present within the polymer carrier compositions in an amount which is effective to reduce local (e.g., on the surface of the polymer carrier) coagulation. It is not intended that the anticoagulant should be present in an amount to have a substantial and prolonged systemic effect in reducing coagulation as is needed in treatment of phlebitis or other clotting events or diseases. The presence of such necessarily large amounts of material would probably be detrimental to the physical properties desired in the polymeric materials of the present invention. It is generally preferred that the anticoagulants be present within the polymer composition as from 0.02 to 10% by weight of solids in the polymer composition. More preferably the composition should comprise from 0.05 to 10% or 0.08 to 8% by weight solids of the anticoagulant. Still more preferably the anticoagulant should comprise from 0.1 to 7.5% by weight or from 0.5 to 7.5% by weight of the polymer solids. The most preferred compositions comprise from 0.75% to 5.0% by weight of the anticoagulants. Mixtures of anticoagulants may be used. It has been found that even where the anticoagulant is water-soluble, such as with heparin, the immersion of the polymer in water during removal of the amine oxide surprisingly should not reduce the level of the heparin in the composition below anticoagulant effective amounts. The amine oxide so strongly forms hydrogen bonds and is so quickly expelled from the polymer composition upon cooling and immersion in water that the partition rate between the heparin and the amine oxide allows the latter to be nearly completely removed without adverse levels of the former being removed. The fact that the heparin forms hydrogen bonds with the cellulose polymer/water-soluble polymer composition in replacement of the hydrogen bonding by the amine oxides further influences the retention of the heparin within the composition during formation. As the composition is hydrolyzed, the heparin is, of course, released into the system along with the hydrolysis products.

The cellulose polymer also tends to resist too ready dissolution by way of random entanglement of the cellulose polymer chains. This entanglement makes dissolution and hydrolysis of that component of the composition more difficult, and serves to entrap the water-soluble polymer component and the anticoagulant within the polymer composition.

Amongst the more recognizable and commercially available anticoagulants are heparin and heparin derivatives and coumarins, such as Dicumarol™, [2H-1-benzopyran-2-one], 3,3-methylenebis[4-hydroxy-coumarin], bis-hydroxycoumarin, Diphenidione, 1H-Indene-1,3(2H)-dione, 2-(diphenylacetyl)-dione, diphenylacetylindandione, Phenindione, 1H-Indene-1,3(2H)-dione, Phenprocoumon, 4-hydroxy-3-(1-phenylpropyl)-2H-1-benzopyran-2-one, 3-(alpha-ethylbenzyl)-4-hydroxycoumarin, 4-hydroxy-3-(3-oxo-1-phenylbutyl)-2H-1-benzopyran-2-one, potassium salt or sodium salt, Heparin Sodium, heparin, Lipo-Hepin™ (Riker), Liquemin Sodium(Organon), enoaparin sodium, FragminTM,deltaprin sodium (a low molecular weight heparin), etc.

The solvents used as the amine oxides of the present invention comprise such materials as N-methylmorpholine-N-oxide, N-methylpiperidine-N-oxide, N-methylpyrrolidine-N-oxide and N-methylazacycloheptane-N-oxide, with the first being more preferred. The preparation of these solvents is described in U.S. Pat. No. 3,447,939.

The basic process of the present invention with respect to the formation of the polymer compositions comprises dissolving the polymeric components and the anticoagulant (and any optional additives) into the amine oxide solvent and then precipitating the polymer composition out of the solvent. The precipitation step may be generally performed by providing the polymeric solution (the cellulose polymer, water-soluble polymer and anticoagulant) into an aqueous environment. The aqueous environment solidifies the polymeric composition and the amine oxide is reduced in its concentration within the polymer. As the amine oxides must usually be heated above room temperature (e.g., to at least about 50° C., and as high as at least 70 or 90 or 110° C.) to dissolve the cellulose material, the aqueous environment and the cooling effect in combination are sufficient to precipitate the polymer and to extract a significant portion of the amine oxide. In fact, the resulting polymers may contain only a trace amount of the amine oxides, if any. These compositions may either be extruded into film form, tube form or other shaped form, preferably directly into an aqueous environment (e.g., water bath) to precipitate the polymer material, harden it, and extract the amine oxide solvent). Extrusion of tube shapes is common in many fields, and merely requires that the extrusion head have a center piece around which the composition is extruded to form the tube. The shapes may also be formed by casting or coat-casting in which the composition is coated on a removable substrate and hardened. The hardened coating is then removed from the casting shape. Fibers may be extruded and then formed into fabrics (e.g., meshes) or films may be punctured or reticulated to form open or porous layers.

Specific uses to which the present technology may be put include vascular replacement materials, coatings for implants, coatings for medical implements (with the coatings being removable so that the entire implement would not have to be discarded), mesh reinforcements, bandages, patches, wrappings, stents, and the like. The use of the polymer compositions of the present invention as vascular replacement structures is particularly preferred.

Typical water soluble polymers include gelatin, polyvinyl alcohol, to polyvinylpyrrolidone, acrylic polymers, and the like. In these various formats, the size, shape, thickness and other characteristics may be varied according to the individual requirements of the intended use. For example, in film form, thickness of from 0.25 mm to 10 mm would be commonly used. For tubular shapes, inside diameters of from 0.5 mm to 10, 15 or 20 mm could be typically used for vascular replacement, wall thickness of from 0.1 or 0.2 mm to 1, 2, 3, or 4 mm could be fabricated. In fabric shapes, fine to medium to thick denier filaments could be used in manufacturing meshes and fabric used in the practice of the present invention. Fiber or filament dimensions of from 0.02 mm or 0.05 mm or 0.1 mm up to 1 or 2 mm could typically be used in the preparation of fibers and filaments in the practice of the present invention.

In addition to the anticoagulants being present in the polymer compositions of the present invention, other materials, either for medical or manufacturing purposes, may be present in the polymer compositions. For example, flexibilizing agents, surfactants, coating aids, lubricating agents, and the like may be present.

FIG. 1 shows a perspective view of a section of vasculature closing element 2 which has a hole 4 and loose prestitching 6 The element 2 has sutures 8 and 10 around the hole 4. An opening 12 is shown at an end of the element 2. In FIG. 1b, two stents 18 and 20 will be positioned to protrude through the hole 4 in the element 2. As shown in FIG. 1c, prestitching 24 and 26 is present around the hole so that after attachment of the of the element 2, the hole 4 may be closed. Ends 28 and 30 of the stents 18 and 20 may be inserted into openings 32 and 34 in the vasculature 40. In FIG. 1d, after insertion of the ends of the stents 28 and 30, sutures 36 and 38 are applied to secure the element 2 to the vasculature 40. FIG. 1e shows the element 2 after securement by stitching 36 and 38 to the vasculature 40. The hole 4 remains open, and the prestitching 6 has not been tightened. FIG. 1f shows the surgically completed connection of the element 3 to the vasculature 40 with the hole 6 closed off by tightened stitching 42.

Figure 1C:
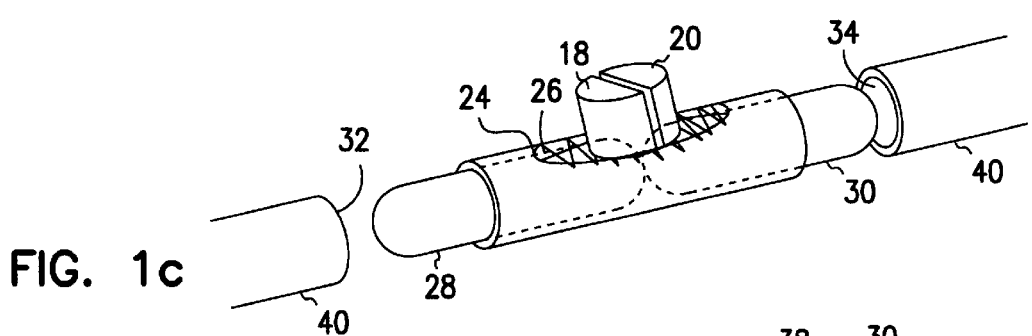
Figure 1D:
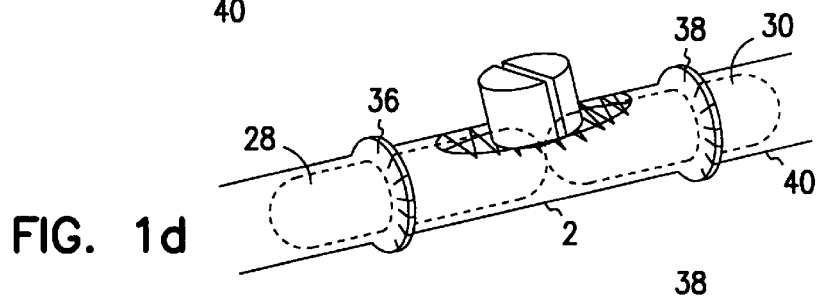
Figure 1E:
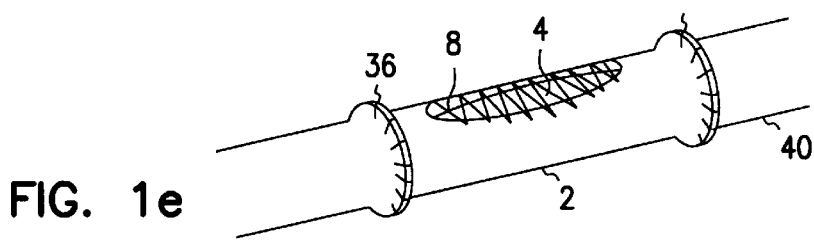
Figure 1F:
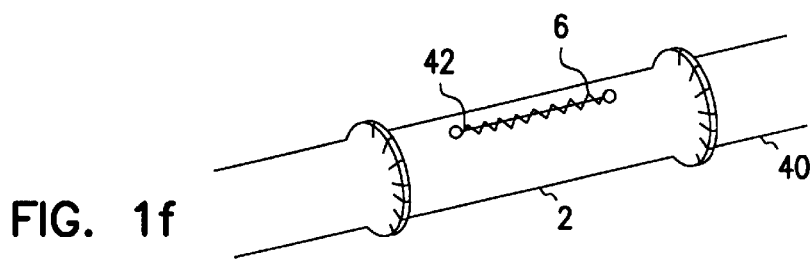
Figure 2:
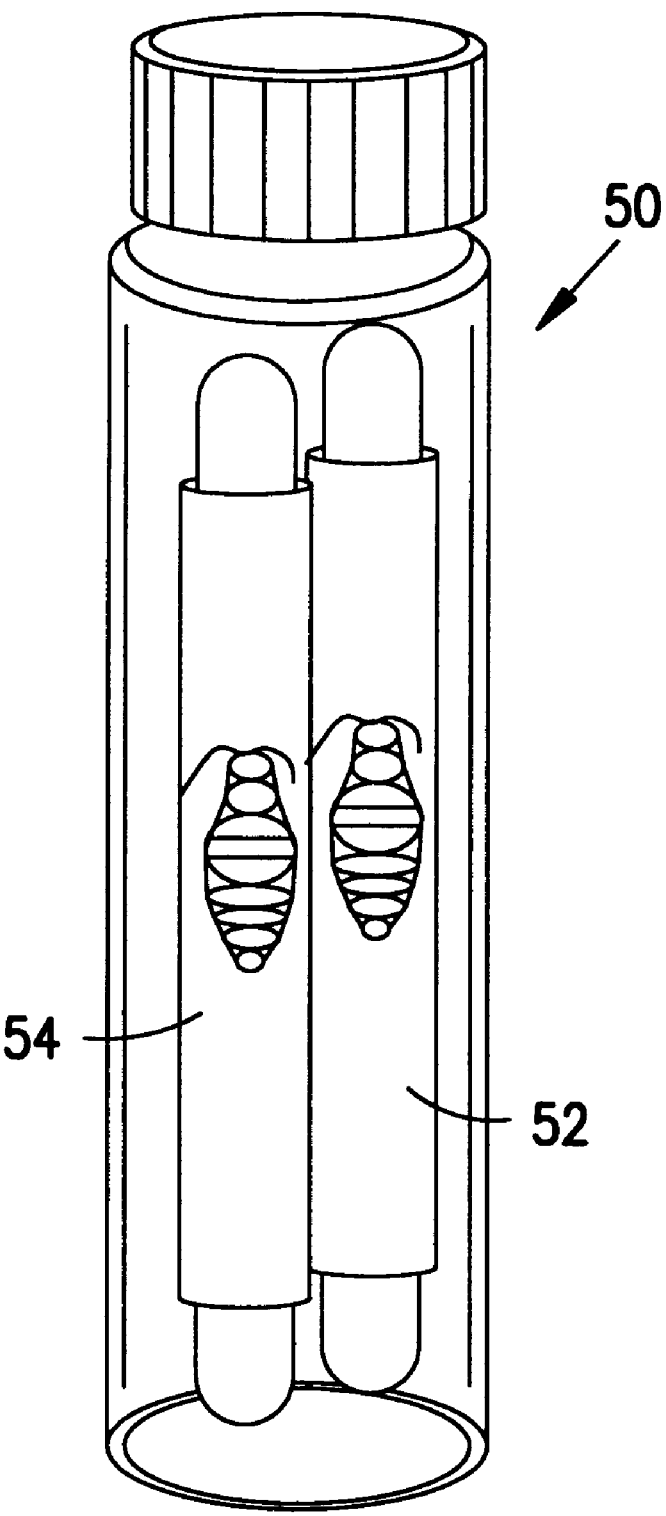
FIG. 2 shows a bottle containing vasculature closing elements according to the presnt invention.

FIG. 2 shows a bottle 50 containing two elements 52 and 54 according to the present invention, as more clearly and individually shown in FIG. 1c.

After attachment of the elements by medical procedure, enastiomosis of the element should continue, with the structural integrity of the element 2 becoming less important. Natural tissue replaces the film material of the element and the hydrolyzed element is absorbed into the body or carried away by the waste stream.

PROPHETIC EXAMPLE

A polymeric composition and extruded tubing for use in vascular replacement could be produced according to the following procedures.

150 grams of N-methylmorpholine-N-oxide is placed into a round-bottom flask and heated in an oil bath at 110° C. with mechanical stirring until melted. While stirring is continued, 6 grams of cellulose fiber (Whatman #4 filter paper which has been defibered in a blender) is added in portions over a 5 minute period. 6 grams of bone gelatin are swelled overnight in 40 ml of water and dissolved in 150 grams of dimethyl sulfoxide. The gelatin solution is added in a stream to the cellulose solution at such a rate as prevents precipitation of the cellulose (about five minutes). The solution is stirred at the elevated temperature until the solution is clear (about 15 minutes). The anticoagulant, e.g., heparin, may be added at this time in small increments, either in solution (e.g., in DMSO, dimethyl sulfoxide) or neat. The amount of heparin to be added would be about 3% of the total weight of solids in the polymer composition. The anticoagulant also could have been previously added to the cellulose solution or the water soluble polymer solution, before combination, during combination or before complete dissolution and blending of the two solutions. While still hot, the solution may be filtered through a sintered glass disk to remove any insoluble particulates. Films may be formed by casting the solution onto a film support (e.g., polyethylene terephthalate) or by extruding the composition through an extrusion head, as into a water bath. A conventional polymeric film extrusion system may be used, keeping the solution or melt temperature sufficiently high to avoid early precipitation of the composition.

What is claimed is:

1. A method for providing a solid article which is haemocompatible comprising:

forming a solution in an amine oxide of a water-soluble polymer capable of hydrogen bonding, a cellulose polymer, and an anticoagulant and reducing the amount of amine oxide in the solution to solidify a solid polymer composition comprising said anticoagulant in said water soluble polymer and said cellulose polymer.

2. The method of claim 1 wherein after reducing the amount of amine oxide in the solution, said water soluble polymer and said cellulose polymer are hydrogen bonded to each other.

3. The method of claim 1 wherein said amine oxide is selected from the group consisting of N-methylmorpholine-N-oxide, N-methylpiperidine-N-oxide, N-methylpyrrolidine-N-oxide and N-methylazacycloheptane-N-oxide.

4. The method of claim 1 wherein said amine oxide comprises N-methylmorpholine-N-oxide.

5. The method of claim 1 wherein said water soluble polymer is selected from the group consisting of gelatin, polyvinyl alcohol, polyvinylpyrrolidone, and acrylic polymers.

6. The method of claim 1 wherein said water soluble polymer comprises gelatin.

7. The method of claim 3 wherein said water soluble polymer comprises gelatin.

8. The method of claim 5 wherein said water soluble polymer comprises gelatin.

9. The method of claim 1 wherein said cellulose polymer comprises plant cellulose.

10. The method of claim 3 wherein said cellulose polymer comprises plant cellulose.

11. The method of claim 5 wherein said cellulose polymer comprises plant cellulose.

12. The method of claim 6 wherein said cellulose polymer comprises plant cellulose.

13. The method of claim 7 wherein said cellulose polymer comprises plant cellulose.

14. The method of claim 1 wherein said solution of water soluble polymer, cellulose polymer and anticoagulant is formed at a temperature above 50° C. and at a temperature above 50° C. said solution is cast or extruded to form a solid composition.

15. The method of claim 14 wherein said solution is extruded to form a tube having an internal diameter of from 0.5 to 20 mm.

16. The method of claim 15 wherein said composition comprises from about 0.05 to 10% by weight of anticoagulant, about 9.9 to 60% by weight water soluble polymer, and from about 30 to 91% by weight cellulose polymer.

17. The method of claim 16 wherein said water soluble polymer comprises gelatin and said anticoagulant comprises heparin.

18. A polymer composition having an anticoagulant distributed therein, said polymer composition comprising a water soluble polymer hydrogen bonded to a cellulose polymer.

19. The polymer composition of claim 18 wherein said composition said water soluble polymer comprises gelatin.

20. The polymer composition of claim 19 wherein said anticoagulant comprises from 0.05 to 10 percent by weight of said polymer composition of heparin.

21. The polymer composition of claim 20 wherein said composition contains trace residue of a cellulose solvent comprising an amine oxide.

22. The polymer composition of claim 18 wherein the anticoagulant is hydrogen bonded into the polymer composition.

23. The polymer composition of claim 22 wherein said anticoagulant comprises heparin.

24. The polymer composition of claim 19 wherein said anticoagulant is hydrogen bonded into said polymer composition.

25. The polymer composition of claim 24 wherein said anticoagulant comprises heparin.

26. The method of providing a solid article which is haemocompatible according to claim 1 comprising:

forming a solution in an amine oxide of a water soluble polymer capable of hydrogen bonding, a cellulose polymer, and an anticoagulant and reducing the amount of amine oxide in the solution to solidify a solid polymer composition comprising said anticoagulant in said water soluble polymer and said cellulose polymer, with hydrogen bonding present between said water soluble polymer and said cellulose polymer, and between the anticoagulant and the water soluble polymer and said cellulose polymer.

27. The method of claim 26 wherein the hydrogen bonding present between the anticoagulant and the water soluble polymer and said cellulose polymer increases the retention of the anticoagulant within the water soluble polymer and said cellulose polymer.

28. The method of claim 26 wherein said anticoagulant is a heparin.

29. The method of claim 27 wherein said anticoagulant is a heparin.

* * * * *